United States Patent
Hayashi et al.

(10) Patent No.: US 9,687,457 B2
(45) Date of Patent: *Jun. 27, 2017

(54) DETRUSOR HYPERACTIVITY WITH IMPAIRED CONTRACTILITY AMELIORATING AGENT

(71) Applicant: TAIHO PHARMACEUTICAL CO., LTD., Chiyoda-ku, Tokyo (JP)

(72) Inventors: Yukio Hayashi, Tsukuba (JP); Takahisa Noma, Tsukuba (JP)

(73) Assignee: Taiho Pharmaceutical Co., Ltd., Chiyoda-ku, Tokyo (JP)

( * ) Notice: Subject to any disclaimer, the term of this patent is extended or adjusted under 35 U.S.C. 154(b) by 1 day.

This patent is subject to a terminal disclaimer.

(21) Appl. No.: 15/155,526

(22) Filed: May 16, 2016

(65) Prior Publication Data

US 2017/0035706 A1 Feb. 9, 2017

Related U.S. Application Data

(63) Continuation of application No. 14/817,318, filed on Aug. 4, 2015.

(51) Int. Cl.
*A61K 31/122* (2006.01)
*A61K 31/12* (2006.01)

(52) U.S. Cl.
CPC .................. *A61K 31/122* (2013.01)

(58) Field of Classification Search
None
See application file for complete search history.

(56) References Cited

U.S. PATENT DOCUMENTS

2015/0094380 A1 4/2015 Hayashi et al.

FOREIGN PATENT DOCUMENTS

| JP | 2002241271 A | 8/2002 |
| JP | 201567565 A | 4/2015 |
| JP | 201586212 A | 5/2015 |
| WO | 99/08987 A1 | 2/1999 |
| WO | 02/066024 A1 | 8/2002 |

OTHER PUBLICATIONS

Goi et al., "Effects of Silodosin, a Selective α1A-Adrenoceptor Antagonist, on Bladder Blood Flow and Bladder Function in a Rat Model of Atherosclerosis Inducted Chronic Bladder ischemia without Bladder Outlet Obstruction", The Journal of Urology, 2013, vol. 190, pp. 1116-1122.

Gomes et al, "Voiding Dysfunction and Urodynamic Abnormalities in Elderly Patients", Rev. Hosp. Clin. Fac. Med. Sao Paulo, 2004, vol. 59, No. 4, pp. 206-215.

(Continued)

*Primary Examiner* — San-Ming Hui
*Assistant Examiner* — Andrew Lee
(74) *Attorney, Agent, or Firm* — Rothwell, Figg, Ernst & Manbeck, P.C.

(57) ABSTRACT

Problem to be Solved by the Invention: To providing a method for ameliorating DHIC.
Means for Solving the Problem: This invention is directed to a treating method for DHIC, comprising the step of administering a therapeutically effective amount of 3-(15-hydroxypentadecyl)-2,4,4-trimethyl-2-cyclohexene-1-one, a salt thereof, or a solvate thereof.

2 Claims, 2 Drawing Sheets

○:Sham group n=11, ●:Control group n=19, ◆:Compound 1 of the present invention group n=8, △:Tamsulosin group n=6
Qmax: maximum urine flow rate, Pdet: detrusor pressure, BC: bladder capacity

(56) References Cited

OTHER PUBLICATIONS

Hashimoto et al., "Effects of the Selective Acetylcholinesterase inhiitor TAK-802 on the Voiding Behavior and Bladder Mass increase in Rats with Partial Bladder Outlet Obstruction", The Journal of Urology, 2005, vol. 174, pp. 1137-1141.

Haylen et al., "An International Urogynecological Association (IUGA)/International Continence Society (ICS) Joint Report on the Terminology for Female Pelvic Floor Dysfunction", Neurourology and Urodynamics, 2010, vol. 29, pp. 4-20.

Kaplan et al., "Tolterodine and Tamsulosin for Treatment of Men with Lower Urinary Tract Symptoms and Overactive Bladder: A Randomized Controlled Trial", JAMA, 2006, vol. 296, No. 19, pp. 2319-2328.

Kwak et al., "Inhibitory effects of propiverine, atropine and oxybutynin on bladder instability in rats with infravesical outlet obstruction", British Journal of Urology, 1998, vol. 82, pp. 272-277.

Maruyama et al., "Effects of ritobegron (KUC-7483), a novel β3-adrenoceptor agonist, on both rat bladder function following partial bladder outlet obstruction and on rat salivary secretion a comparison with the effects of tolterodine", Journal of Smooth Muscle Research, 2012, vol. 48, No. 5&6 pp. 115-124.

Osman et al., "Detrusor Underactivity and the Underactive Bladder: A New Clinical Entity? A Review of Current Terminology, Definitions, Epidemiology, Aetiology, and Diagnosis", European Urology, 2014, vol. 65, pp. 389-398.

Resnick et a., "Detrusor Hyperactivity with Impaired Contractile Function", JAMA, 1987, vol. 257, No. 22, pp. 3076-3081.

Schäfer et al., Principles and Clinical Application of Advanced Urodynamic Analysis of Voiding Functioning, Urologic Clinics of North America, 1990, vol. 17, No. 3, pp. 553-566.

Kokubun et al., Denervation and Bladder Smooth Muscle Contraction Disorder in an Obstructed Bladder—Denervation and Preventing Effect of Cyclohexenone Derivative, Japanese Journal of Urology, 2011, vol. 102, No. 2, p. 352, OP-069, I .13-14.

Nomiya et al., A Neurotrophic Agent, N-Hexacosanol, Prevents the Development of Bladder Hyperactivity in a Rat Model of Chronic Bladder Ischemia, J. Urology, 2015, vol. 193, No. 4S Supplement, p. e77, MP8-12.

Saito et al., Effect of Cyclohexenonic Long-chain Fatty Alcohol on Rat Overactive Bladder Induced by Bladder Neck Obstruction, Eur. J. Pharmacol., 2004, vol. 501, pp. 143-149, Abstract, p. 1442.1., p. 146 3.1, 3.2., Table 1, Table 2.

Watanabe et al., Effects of Long-Chain Fatty Alcohol on Peripheral Nerve Conduction and Bladder Function in Diabetic Rats, Life Sciences, 2002, vol. 70, pp. 2215-2224, Abstract, p. 2216 para. 3-4, p. 2217-I. 4-5.

Sham

Control

○:Sham group n=11, ●:Control group n=19, ◆:Compound 1 of the
present invention group n=8, △:Tamsulosin group n=6
Qmax: maximum urine flow rate, Pdet: detrusor pressure, BC:
bladder capacity

DETRUSOR HYPERACTIVITY WITH IMPAIRED CONTRACTILITY AMELIORATING AGENT

CROSS REFERENCE TO RELATED APPLICATION

This application is a continuation of U.S. Ser. No. 14/817,318 filed Aug. 4, 2015, the disclosure of which is incorporated herein in its entirety by reference.

TECHNICAL FIELD

The present invention relates to a method for treating detrusor hyperactivity with impaired contractility (hereinafter referred to as "DHIC"), comprising the step of administering a therapeutically effective amount of 3-(15-hydroxypentadecyl)-2,4,4-trimethyl-2-cyclohexene-1-one, a salt thereof, or a solvate thereof.

BACKGROUND ART 3-(15-hydroxypentadecyl)-2,4,4-trimethyl-2-cyclohexene-1-one (hereinafter referred to as "Compound 1 of the present invention") is a compound having a structure represented by Formula (1) below.

[Chem. 1]

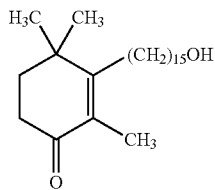

(1)

Patent Document 1 discloses that a cyclohexenone long-chain alcohol comprising the compound represented by Formula (1) has an effect of promoting neurite growth, and thus is useful as a preventive and/or therapeutic agent for brain disorders such as dementia. Patent Document 2 discloses that a cyclohexenone long-chain alcohol comprising the compound represented by Formula (1) is useful as a therapeutic agent for treating dysuria.

However, the effect as a therapeutic agent for treating dysuria shown in Patent Document 2 was confirmed only against dysuria with depressed bladder function (the effect was confirmed by the improvement in maximum voided volume, bladder capacity, and micturition efficiency). More specifically, the effect of ameliorating detrusor hyperactivity with impaired contractility of Compound 1 of the present invention has been completely unknown.

In normal micturition function, detrusor doesn't contract during storage phase (urine can be reserved in bladder), and contracts during only voiding phase. In storage dysfunction disease (overactive bladder), detrusor overactive occurs during storage phase, so, urine can't be reserved fully in bladder. Medicines, such as an anti-cholinergic agent and a β3 receptor agonist, are effective for storage dysfunction disease. While on the other hand, in urine-voiding dysfunction disease (underactive bladder), an increased residual urine volume is a problem. Medicines, such as a cholinesterase inhibitor and a cholinergic agonist, are used for urine-voiding dysfunction disease. However, it is generally known that an effective agent for overactive bladder does not work or is even detrimental against underactive bladder (Non-patent Document 1, Non-patent Document 2). Also, it is known that an effective agent for underactive bladder is invalidity or detrimental against overactive bladder (Non-patent Document 3). In these ways, although there are some therapeutic approaches against an individual disease of overactive bladder or underactive bladder, there is merely agent to be expected effective against both overactive bladder and underactive bladder.

DHIC is a disorder which presents both of detrusor overactive and detrusor impaired contractility in the body of the same individual (Non-patent Document 4, Non-patent Document 5). Because detrusor overactive occurs additionally with a residual urine volume increased by detrusor impaired contractility, it induces high-pressure during storage phase and incontinence. Further, if such condition is left unattended without appropriate care, it results in a sever disease such as urinary-tract infection, upper urinary tract disorder, or renal dysfunction.

DHIC is clinically diagnosed by confirming coexistence of detrusor overactive during storage phase and detrusor impaired contractility during voiding phase using Pressure-Flow Study (nomogram analysis is useful for the diagnosis) (Non-patent Document 4, Non-patent Document 5).

Also, because DHIC is disorder which presents both of detrusor overactive and detrusor impaired contractility, the diagnosis of overactive bladder and underactive bladder can be available for diagnosis of DHIC (Non-patent Document 6, Non-patent Document 7). Those are, overactive bladder is diagnosed by subjective symptom (urgency, incontinence, pollakiuria etc.), and underactive bladder is diagnosed by subjective symptom (forceless urinary stream, terminal dribbling, retarded micturition, abdominal straining to urinate, a feeling of residual urine, urinary retention etc.), uroflowmetry, and measurement of residual urine volume etc. Then DHIC can be diagnosed by confirming coexistence of both the disorders.

In therapeutic strategy for DHIC, because conflicting dysfunctions of detrusor overactive and detrusor impaired contractility coexist in the body of the same individual, it is therapeutic high-difficult dysuria. As described above, generally, the ameliorating agent with only either of overactive bladder or underactive bladder was clinically insufficient effect against patients with DHIC.

Considering this situation, we need the therapeutic agent for DHIC which presents both of detrusor overactivity and detrusor impaired contractility in the body of the same individual. It was recently reported that an α1-blocker such as Tamsulosin etc., which was effective on urine-voiding dysfunction (underactive bladder), was also effective on overactive bladder (Non-patent Document 8).

CITATION LIST

Patent Documents

Patent Document 1: International Publication WO1999/008987
Patent Document 2: International Publication WO2002/066024

Non-patent Documents

Non-patent Document 1: J Smooth muscle Res 48, p 115-124 (2012)
Non-patent Document 2: Br J Urol 82, p 272-277 (1998)

Non-patent Document 3: J Urol 174, p 1137-1141 (2005)
Non-patent Document 4: JAMA, 257, p 3076-3081 (1987)
Non-patent Document 5: Rev Hosp Clin Fac Med Sao Paulo, 59, p 206-215 (2004)
Non-patent Document 6: Neurourol Urodyn, 29, p 4-20 (2010)
Non-patent Document 7: Eur Urol, 65, p 389-398 (2014)
Non-patent Document 8: JAMA 296, p 2319-2328 (2006)

SUMMARY OF INVENTION

Technical Problem

An object of the present invention is to provide a method for treating DHIC by improving both of detrusor overactivity and detrusor impaired contractility.

Solution to Problem

The inventors of the present invention carried out extensive research to attain the above object, and found that 3-(15-hydroxypentadecyl)-2,4,4-trimethyl-2-cyclohexene-1-one represented by Formula (1) below ameliorates both of detrusor overactivity and detrusor impaired contractility, and thus is useful as a therapeutic agent for treating a disorder based on DHIC.

[Chem. 1]

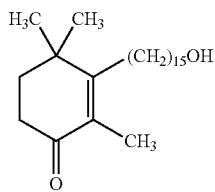

(1)

More specifically, the present invention provides a method for treating a disorder that presents both detrusor overactivity and detrusor impaired contractility, comprising the step of administering a therapeutically effective amount of 3-(15-hydroxypentadecyl)-2,4,4-trimethyl-2-cyclohexene-1-one, a salt thereof, or a solvate thereof.

Further, the present invention provides a method for treating DHIC, comprising the step of administering a therapeutically effective amount of 3-(15-hydroxypentadecyl)-2,4,4-trimethyl-2-cyclohexene-1-one, a salt thereof, or a solvate thereof, to a patient with DHIC.

Further, the present invention provides a method of ameliorating a disease that presents both of detrusor underactivity and detrusor hyperactivity, using 3-(15-hydroxypentadecyl)-2,4,4-trimethyl-2-cyclohexene-1-one, a salt thereof, or a solvate thereof, to a patient that presents both of detrusor underactivity and detrusor hyperactivity.

Advantageous Effects of Invention

The present invention enables effective treatments of DHIC.

Figure 1:
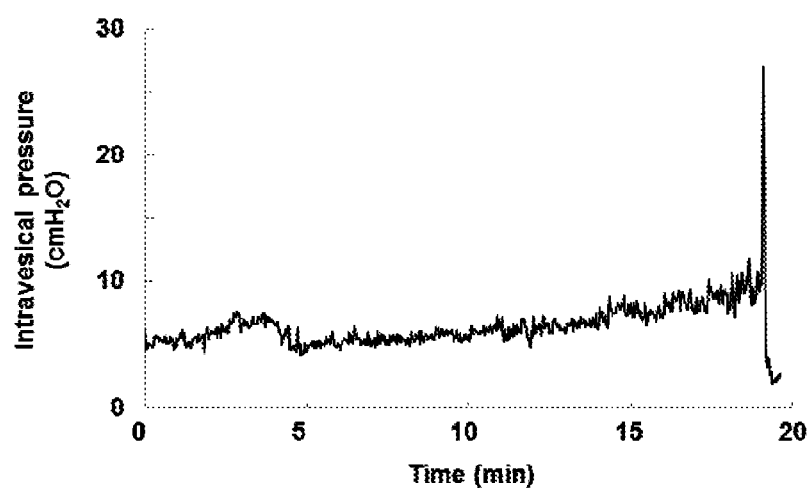
FIG. 1 shows representative cystometry charts of rat dysuria model that presents DHIC.
Figure 1:
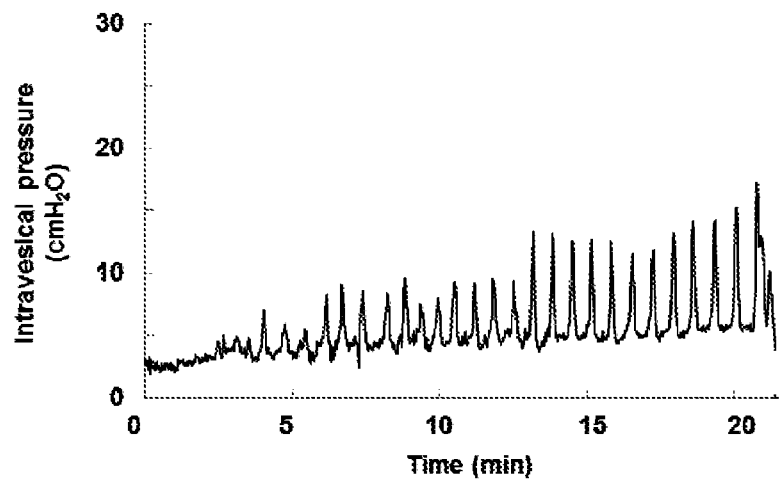

Sham: n=11, Control (6% Gelucire): n=19,
Compound 1 of the present invention (10 mg/kg×2/day p.o.): n=8, Tamsulosin (0.3 mg/kg, i.v.): n=6

DESCRIPTION OF EMBODIMENTS

Compound 1 of the present invention is a known compound, and is produced by, for example, the method disclosed in International Publication WO1999/008987.

The term "treatment" in the present invention means maintenance treatment for alleviating the symptoms and preventing the recurrence by improving a disease that presents both of detrusor overactivity and detrusor underactivity, especially, maintenance treatment for alleviating the symptoms and preventing the recurrence by ameliorating DHIC.

In the present specification, the phrase "a treatment of DHIC" means a method of ameliorating a disease that presents both of detrusor overactivity during storage phase and detrusor impaired contractility during voiding phase.

Compound 1 of the present invention may be formed acid adduct salt, or base adduct salt. And the present include the present invention to the extent that the salt is a pharmaceutically acceptable salt thereof. Specifically, it includes an acid adduct salt with an inorganic acid such as hydrochloric acid, hydrobromic acid, hydroiodic acid, sulfuric acid, nitric acid, or phosphoric acid etc.; an acid adduct salt with an organic acid such as formic acid, acetic acid, propionic acid, oxalic acid, malonic acid, succinic acid, fumaric acid, maleic acid, lactic acid, malic acid, citric acid, tartaric acid, carbonic acid, picric acid, methansulfonic acid, p-toluenesulfonic acid, or glutamic acid etc.; salt with an inorganic base such as sodium, potassium, magnesium, calcium, or aluminum etc.; salt with an organic base such as methylamine, ethylamine, meglumine, or ethanolamine etc.; salt with basic amino acid such as lysine, arginine, or ornithine; ammonium salt etc.

Examples of the solvent of the solvate of Compound 1 of the present invention include water, methanol, ethanol, isopropanol, acetonitrile, tetrahydrofuran, ethyl acetate, toluene, hexane, acetone, methyl ethyl ketone, and methyl isobutyl ketone etc.

3-(15-hydroxypentadecyl)-2,4,4-trimethyl-2-cyclohexene-1-one, a salt thereof, or a solvate thereof of the present invention can be prepared into various dosage forms by using known preparation methods using a pharmaceutically acceptable carrier. The dosage form is not particularly limited, and examples thereof include oral agents such as tablets, coated tablets, pills, powdered drugs, granules, capsules, liquids, suspensions, or emulsions; and parenteral agents such as injections or suppositories.

In preparing tablets, examples of carrier include excipients such as lactose, sucrose, sodium chloride, glucose, urea, starch, calcium carbonate, kaolin, crystalline cellulose, or silicic acid; binders such as water, ethanol, propanol, cornstarch, simple syrup, glucose solution, starch solution, gelatin solution, carboxymethylcellulose, shellac, methylcellulose, hydroxypropylcellulose, hydroxypropylmethylcellulose, potassium phosphate, or polyvinyl pyrrolidone; disintegrants such as dry starch, sodium alginate, powdered agar, powdered laminaran, sodium hydrogencarbonate, calcium carbonate, polyoxyethylene sorbitan fatty acid ester, sodium lauryl sulfate, stearic acid monoglyceride, or lactose; disintegration inhibitors such as sucrose, stearic acid, cacao butter, or hydrogenated oils; absorbefacients such as quaternary ammonium salts or sodium lauryl sulfate; moisturizers such as glycerin or starch; adsorbents such as starch, lactose, kaolin, bentonite, or colloidal silicic acid; and lubricants such as purified talc, stearate, boric acid powder, or polyethylene glycol. Further, the tablets may be generally coated tablets such as sugar-coated tables, gelatin-coated tablets, enteric-coated tablets, film-coated tablets, double-coated tablets, or multi-coated tablets.

In preparing pills, examples of the carrier include excipients such as glucose, lactose, starch, cacao butter, hardened vegetable oil, kaolin, or talc; binders such as gum arabic powder, tragacanth powder, gelatin, or ethanol; and disintegrators such as laminaran or agar. Capsules are usually prepared in a standard method by blending the drug with one or more carriers as exemplified above, and encapsulating the mixture into hard gelatin capsules, soft capsules, etc.

In preparing oral liquid formulations, an internal liquid medicine, a syrup, an elixir, or the like, may be prepared by a standard method using sweetening/flavoring agent, buffer, stabilizer, etc. In this case, examples of sweetening/flavoring agents include sucrose, wild orange peel, citric acid, and tartaric acid; examples of buffers include sodium citrate; and examples of stabilizers include tragacanth, gum arabic, and gelatin.

In preparing suppositories, examples of usable carriers include polyethylene glycol, cacao butter, higher alcohols, esters of higher alcohols, gelatin, and semisynthetic glycerides.

In preparing injections, the liquids, emulsions, and suspensions are preferably sterilized and rendered isotonic to the blood. Examples of diluents for preparing such dosage forms include water, aqueous lactic acid solution, ethanol, propylene glycol, macrogols, ethoxylated isostearyl alcohol, polyoxyethylenated isostearyl alcohol, and polyoxyethylene sorbitan fatty acid ester.

In this case, sodium chloride, glucose, or glycerin in an amount sufficient to prepare an isotonic solution may be added to the pharmaceutical formulation. Further, general solubilizers, buffers, anesthetics, and the like, may also be added to the pharmaceutical formulation. Additionally, coloring agents, preservatives, aromatics, flavors, sweetening agents, or other medicinal products may be incorporated, if necessary, into the pharmaceutical formulations.

The method for administering the DHIC ameliorating agent of the present invention is not particularly limited, and is suitably selected according to the dosage form thereof, the age, gender, and other conditions of the patient, the severity of the symptoms of the patient, and the like. For example, tablets, pills, powdered drugs, granules, capsules, liquids, suspensions, and emulsions are orally administered. The injections are intravenously administered singly, or as a mixture with a general infusion liquid such as liquid glucose or an amino acid liquid. Further, as necessary, the injections are singly administered intra-arterially, intramuscularly, intradermally, subcutaneously, or intraperitoneally. The suppositories are intrarectally administered.

The amount of the compound of the present invention or a salt thereof to be incorporated into each of the above dosage unit form depends on the symptoms of the target patient, or depends on the drug form; however, the amount per dosage unit form is generally preferably about 0.005 to 1,000 mg, more preferably 1 to 800 mg, further preferably 5 to 500 mg for oral agents; about 0.001 to 500 mg, more preferably 0.02 to 400 mg, further preferably 1 to 250 mg for injections; and about 0.01 to 1,000 mg, more preferably 1 to 800 mg, further preferably 5 to 500 mg for suppositories. Additionally, the daily dose for an adult of the drug to be administered with the above dosage form is generally about 0.005 to 5,000 mg, preferably 0.01 to 2,000 mg, more preferably 10 to 1600 mg, further preferably 20 to 800 mg, although such doses depend on the symptom, body weight, age, gender, etc., of the patient. For each day, the daily dose is preferably taken at one time, or divided into two to four administrations.

The present invention is more specifically described below in reference to the Test Examples; however, the present invention is not limited to these examples.

EXAMPLES

Test Example 1

Preparation of Rat Model that Presents DHIC

The models were produced by partial ligation (φ1.57 mm) of urethra in rats (9 weeks, female, Sprague-Dawley). Six weeks after preparation of the model, the rats were released the ligation. The next day, the intravesical pressure and the voided volume were measured under awake condition. And the detrusor contractility during voiding phase was evaluated by nomogram analysis using Qmax and Pdet. Additionally, the detrusor overactivity, as index of overactive bladder, and the increase of residual urine volume, as index of underactive bladder, were evaluated.

FIG. 1 shows representative cystometry charts. In the dysuria model rat (control) compared to sham rat, there is the characteristics of detrusor hyperactivity with impaired contractility that are characterized by remarkable overactivity and increased residual urine volume (Table 1).

TABLE 1

The effects of Compound 1 of the present invention and α1-blocker (Tamsulosin) on detrusor overactivity and residual urine volume in rat dysuria model that presents DHIC.

| Group | n | Detrusor overactivity (times/min) | Residual urine volume (mL) |
|---|---|---|---|
| Sham | 11 | 0.19 ± 0.09 | 0.10 ± 0.03 |
| Control | 19 | 1.73 ± 0.10 # | 0.57 ± 0.06 # |
| Compound 1 of the present invention | 8 | 0.63 ± 0.10* | 0.28 ± 0.13* |
| Tamsulosin | 6 | 0.68 ± 0.33 § | 0.64 ± 0.08 |

\#: $p < 0.05$ vs. Sham group (unpaired Student's t-test)
*$p < 0.05$ vs. Control group (unpaired Student's t-test)
§: $p < 0.05$ vs. Control group (unpaired Student's t-test)

Figure 2:
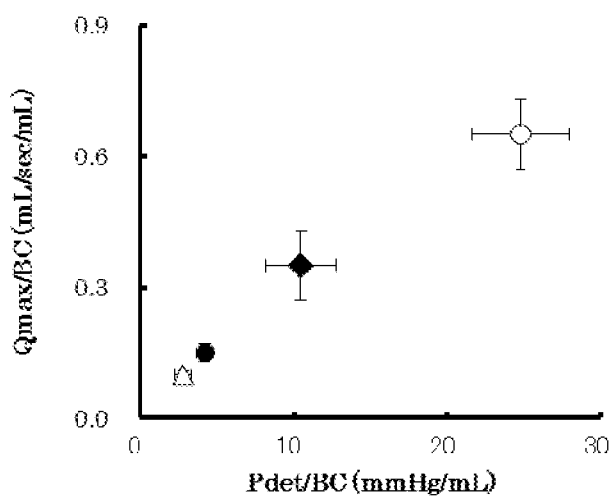
FIG. 2 shows the effects of Compound 1 of the present and α1-blocker (Tamsulosin) on detrusor contractility in rat dysuria model that presents DHIC.

Through evaluation of detrusor contractility during voiding phase in refer to nomogram analysis which are used in clinical sites (Non-patent Document 9: Urol Clin North Am, 17, p 553-566 (1990)), because the plot of control group is positioned in a position relatively close to the origin compared to it of sham group (the distance from the origin: Sham group 24.75±3.14, control group 4.24±0.53, p<0.05), it is judged that reduction of detrusor contractility occurs in the rat dysuria model (FIG. 2).

In the rat dysuria model from these findings, it is confirmed that the detrusor overactivity during storage phase and the reduction of detrusor contractility during voiding phase in nomogram analysis coexist in the body of the same individual which is clinical diagnostic index of DHIC. It is found that the rat dysuria model is able to be evaluated as model of DHIC.

Test Example 2

Effects of Ameliorating Detrusor Overactivity and Detrusor Impaired Contractility in Rat Dysuria Model that Presents DHIC The effect of 3-(15-hydroxypentadecyl)-2,4,4-trimethyl-2-cyclohexene-1-one (hereinafter referred to as "Compound 1 of the present invention") on DHIC was evaluated.

The dysuria models in this example were prepared in the same manner as in Test Example 1. The test drugs (vehicle: 6% Gelucire, Compound 1 of the present invention 10 mg/kg) were orally administered to each group after two weeks from the preparation of the models twice a day for four weeks. On the day of the final administration, the rats were released the ligation of urethra. The next day, the intravesical pressure and the voided volume were measured using cystometry under conscious condition. The detrusor overactivity, as an index of overactive bladder, and the increase of residual urine volume, as an index of underactive bladder, were evaluated. Additionally, the detrusor contractility during voiding phase was evaluated by nomogram analysis using Qmax and Pdet.

In comparison with the detrusor overactivity ($1.73 \pm 0.10$ times/min) and the residual urine volume ($0.57 \pm 0.06$ mL) in control group receiving vehicle (6% Gelucire), detrusor overactivity ($0.63 \pm 0.14$ times/min) and residual urine volume ($0.28 \pm 0.13$ mL) in the group receiving Compound 1 of the present invention were significantly improved (Table 1). Additionally, from the result of evaluation using nomogram analysis, because the plot of Compound 1 of the present invention group is positioned in a position relatively distant from the origin compared to it of control group (the distance from the origin: $10.5 \pm 2.3$, $p<0.05$), it is judged that detrusor contractility is improved in Compound 1 of the present invention group compared to control group (FIG. 2).

In DHIC model that detrusor overactivity and detrusor impaired contractility coexist, it is recognized that Compound 1 of the present invention possesses effect for ameliorating both of detrusor overactivity and detrusor impaired contractility.

Comparative Example 1

Effects of α1-Blocker (Tamsulosin) on Detrusor Overactivity and Detrusor Underactivity/Impaired Contractility in Rat Dysuria Model that Presents DHIC In the same manner as Test Example 1, the rats were released the ligation of urethra at six weeks after the preparation of the model. The next day, the intravesical pressure and the voided volume were measured using cystometry under conscious condition. The detrusor overactivity, as an index of overactive bladder, and the increase of residual urine volume, as an index of underactive bladder, were evaluated. Additionally, the detrusor contractility during voiding phase was evaluated by nomogram analysis using Qmax and Pdet. Tamsulosin (3 μg/kg) was administered intravenously to the dysuria rat at the evaluation (six weeks after preparation of the model).

Detrusor overactivity was significantly improved in Tamsulosin (3 μg/kg) group ($0.68 \pm 0.33$ times/min) than control group ($1.73 \pm 0.10$ times/min) (Table 1). However, Tamsulosin (3 μg/kg) has no effect on residual urine volume (Table 1) and detrusor contractility in nomogram analysis (FIG. 2).

Comparative Example 2

Effects of α1 Blocker (Tamsulosin) on Detrusor Impaired Contractility in Rat Underactive Bladder Model The effects of α1 blocker (Tamsulosin) on underactive bladder were evaluated. The dysuria models in the present example were prepared by treating 10-week-old female Wistar rats with streptozotocin (65 mg/kg, i.p.). From four weeks after the preparation of the models, Tamsulosin (1 μg/kg/hr) was administered subcutaneously using osmotic pump. Four weeks after the implant of osmotic pump, the intravesical pressure and the voided volume were measured using cystometry under urethane anesthesia condition. And the residual urine volume, as an index of underactive bladder, was evaluated.

Table 2 shows the results. In comparison with the Sham group, significant increase of the residual urine volume, which is an index of underactive bladder, was observed in the control group (eight weeks after the development of the disease in the models). Tamsulosin showed significant reduction on the increase of residual urine volume which was observed in the control group.

The above results suggest that Tamsulosin improves underactive bladder, that is, detrusor impaired contractility.

TABLE 2

Effects of α1 blocker (Tamsulosin) on residual urine volume in rat underactive bladder model

| Group | n | Residual urine volume (mL) |
|---|---|---|
| Control | 10 | $1.11 \pm 0.20$ |
| Tamsulosin | 9 | $0.47 \pm 0.11$ § |

§: $p < 0.05$ vs. Control group (unpaired Student's t-test)

Although an α1blocker, which generally are used as dysuria-treating drug, has effect on underactive bladder (Comparative Example 2) and are also reported effect for improving overactive bladder (Non-patent Document 10: J Urol, 190, p 1116-1122 (2013)), the effect of Tamsulosin was not observed in dysuria (DHIC) that detrusor overactivity and detrusor impaired contractility coexist in the body of the same individual (Comparative Example 1).

On the other hand, Compound 1 of the present invention shows effect for ameliorating both dysfunctions in DHIC that detrusor overactivity and detrusor impaired contractility coexist (Test Example 2). Therefore, it is suggested that Compound 1 of the present invention is a useful therapeutic agent for DHIC (Test Example 2).

The invention claimed is:
1. A method for treating a disorder that presents both detrusor overactivity and detrusor impaired contractility, comprising the step of administering a therapeutically effective amount of 3-(15-hydroxypentadecyl)-2,4,4-trimethyl-2-cyclohexene-1-one, a salt thereof, or a solvate thereof.
2. A method for treating detrusor hyperactivity with impaired contractility, comprising the step of administering a therapeutically effective amount of 3-(15-hydroxypenta- decyl)-2,4,4-trimethyl-2-cyclohexene-1-one, a salt thereof, or a solvate thereof, to a patient with detrusor hyperactivity with impaired contractility.

* * * * *